US00PP34836P3

(12) United States Plant Patent
Blom

(10) Patent No.: US PP34,836 P3
(45) Date of Patent: Dec. 13, 2022

(54) ***HEMEROCALLIS* PLANT NAMED 'VER00330'**

(50) Latin Name: ***Hemerocallis* hybrid**
Varietal Denomination: 'VER00330'

(71) Applicant: Heemskerk Vasteplanten BV, Noordwijk (NL)

(72) Inventor: Arie Blom, Vleuten (NL)

(73) Assignee: HEEMSKERK VASTEPLANTEN BV, Noordwijk (NL)

( * ) Notice: Subject to any disclaimer, the term of this patent is extended or adjusted under 35 U.S.C. 154(b) by 0 days.

(21) Appl. No.: 17/670,974

(22) Filed: Feb. 14, 2022

(65) Prior Publication Data

US 2022/0264781 P1 Aug. 18, 2022

(30) Foreign Application Priority Data

Feb. 15, 2021 (QZ) ..... 20210216

(51) Int. Cl.
*A01H 5/02* (2018.01)
*A01H 6/56* (2018.01)

(52) U.S. Cl.
USPC ..... Plt./312
CPC ..... *A01H 6/56* (2018.05)

(58) Field of Classification Search
USPC ..... Plt./312
CPC ... A01H 5/02; A01H 5/00; A01H 5/12; A01H 6/00; A01H 6/56
See application file for complete search history.

(56) References Cited

PUBLICATIONS

CPVO Register 4.1.47, retrieved on Mar. 29, 2022 at https://online.plantvarieties.eu/publicConsultationDetails?registerId=20210216&denomination=ver00330, 2 pp. (Year: 2022).*

* cited by examiner

*Primary Examiner* — June Hwu
(74) *Attorney, Agent, or Firm* — Penny J. Aguirre

(57) ABSTRACT

A new cultivar of *Hemerocallis* plant named 'VER00330' that is characterized by its flowers and flower buds that are dark red in color, its long and continuous blooming habit; blooming from the end of June to the end of September in the Netherlands, its compact plant habit, and its deciduous growth habit (dormant in winter).

3 Drawing Sheets

Botanical classification: *Hemerocallis* hybrid.
Cultivar Designation: 'VER00330'.

CROSS-REFERENCE TO A RELATED APPLICATION

This application claims priority to European Community Plant Variety Office (CPVO) Plant Breeder's Rights Application No. 2021/0216 filed on Feb. 15, 2021, under 35 U.S.C. 119(f), the entire contents of which is incorporated by reference herein.

BACKGROUND OF THE INVENTION

The present invention relates to a new and distinct cultivar of *Hemerocallis* plant of hybrid origin, botanically known as *Hemerocallis* 'VER00330' and will be referred to hereafter by its cultivar name, 'VER00330'. 'VER00330' is a new cultivar of herbaceous daylily grown for use in the landscape and as a container plant.

The new cultivar was developed through an on-going breeding program conducted by the Inventor in Noordwijk, The Netherlands. The objectives of the breeding program are to develop new cultivars of *Hemerocallis* with long and continuous blooming habits combined with compact and clump forming plant habits.

The new cultivar arose from a crosses made in 2014. The new cultivar arose from open pollination of an unpatented and unnamed proprietary plant from the Inventor's breeding program, designation HEM 2006/2007-021, as the female parent. The male parent is unknown. 'VER00330' was selected as a single unique plant from the resulting seedlings in 2016.

Asexual propagation of the new cultivar was first accomplished by division in Noordwijk, The Netherlands in 2018 by the Inventor. Asexual propagation by division has determined that the characteristics of this cultivar are stable and are reproduced true to type in successive generations.

SUMMARY OF THE INVENTION

The following traits have been repeatedly observed and represent the characteristics of 'VER00330'. These attributes in combination distinguish 'VER00330' as a new and distinct cultivar of *Hemerocallis*.

1. 'VER00330' exhibits flowers and flower buds that are dark red in color.
2. 'VER00330' exhibits a long and continuous blooming habit; blooming from the end of June to the end of September in the Netherlands.
3. 'VER00330' exhibits a compact plant habit.
4. 'VER00330' exhibits a deciduous growth habit (dormant in winter).

The female parent of 'VER00330' differs from 'VER00330' in having flower buds that are green-yellow in color, flowers that are light red in color, and leaves that are more narrow. The new cultivar can be most closely compared to *Hemerocallis* cultivars 'VER00322' (U.S. Plant Pat. No. 29,136) and 'VER00198' (U.S. Plant Pat. No. 27,004). 'VER00322' is similar to 'VER00330' in having a dormant growth habit in winter, a long flowering period, and flowers that are red in color. 'VER00322' differs from 'VER00330' in having flowers that are lighter red in color, a later flowering season, less fertility, and flower buds that are green-yellow in color. 'VER00198' is similar to 'VER00330' in having a dormant growth habit in winter, a long flowering period, and floriferous blooming habit. 'VER00198' differs from 'VER00330' in having flowers that are pink in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but are not limited to publications from European plant trials.

BRIEF DESCRIPTION OF THE DRAWINGS

The accompanying color photographs illustrate the overall appearance and distinct characteristics of the new *Hemerocallis*. The photographs were taken of a 12-month-old plant as grown in a conventional greenhouse with lightly chalked glass in a 17-cm container in Noordwijk, The Netherlands.

The photograph in FIG. 1 provides a side view of 'VER00330' in bloom.

Figure 1:
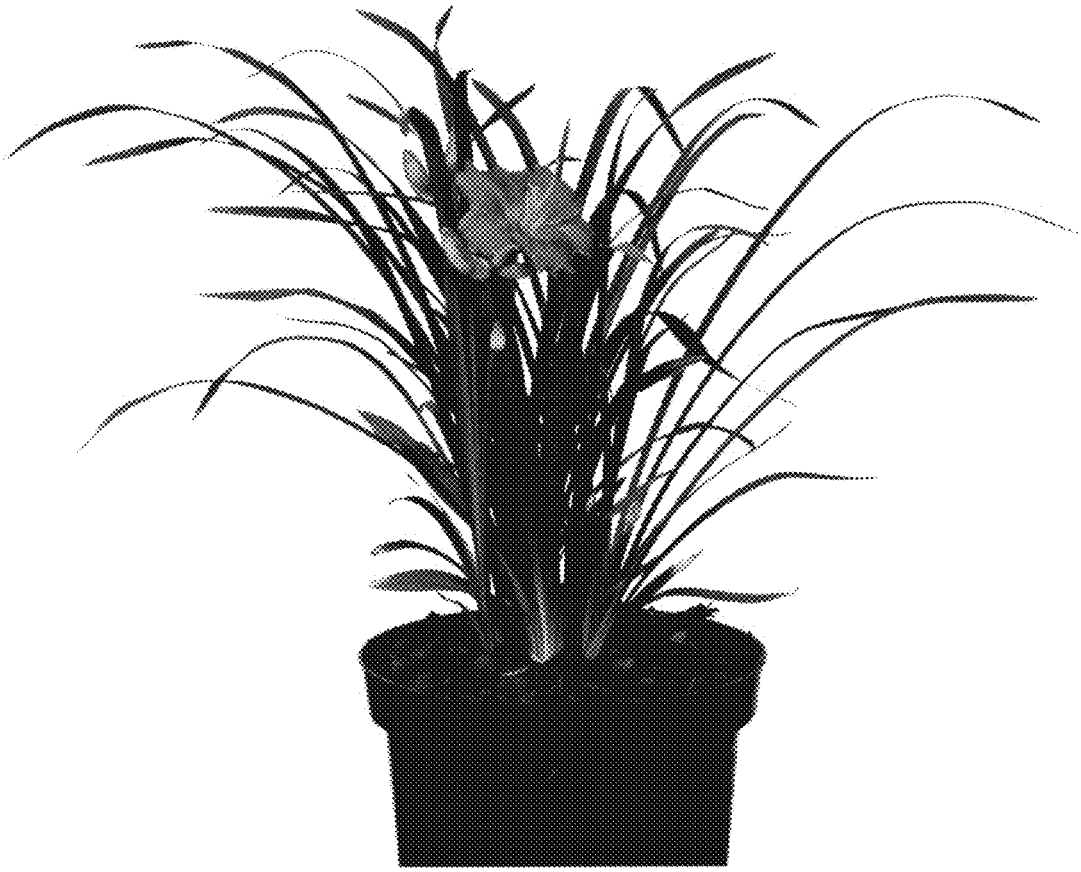
Figure 2:
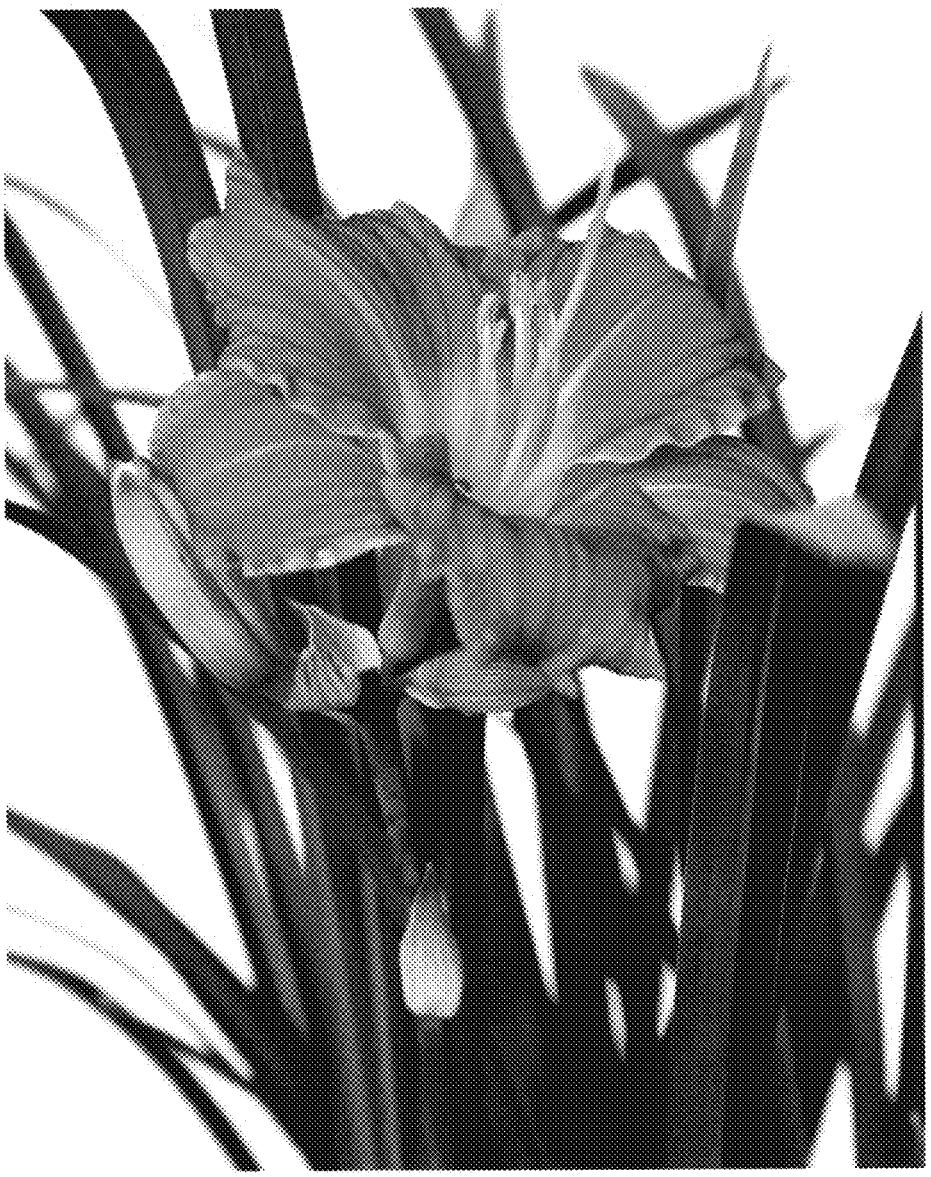

The photograph in FIG. 2 provides a close-up view of a flower of 'VER00330'.

Figure 3:
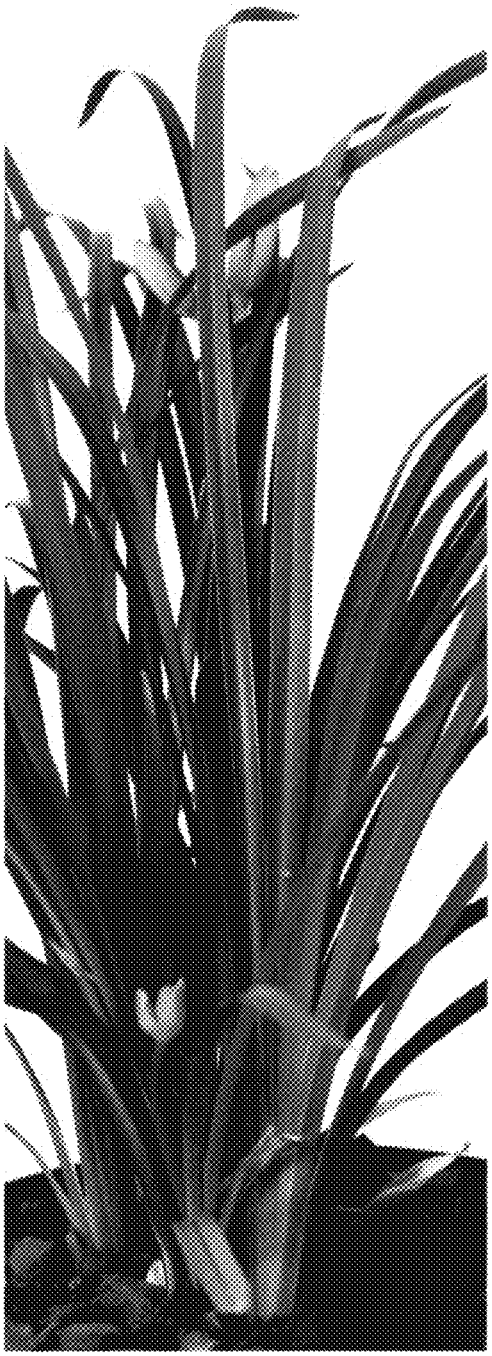

The photograph in FIG. 3 provides a close-up view of the foliage of 'VER00330'.

The colors in the photographs are as close as possible with the digital photography and printing techniques utilized and the color codes in the detailed botanical description accurately describe the new *Hemerocallis*.

DETAILED BOTANICAL DESCRIPTION OF THE PLANT

The following is a detailed description of 12-month-old plants of the new cultivar as grown in a conventional greenhouse with lightly chalked glass in 17-cm containers in Noordwijk, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General characteristics:

*Blooming period*.—End of June to the end of September in The Netherlands.

*Plant type*.—Herbaceous perennial.

*Plant habit*.—Compact, upright with arching leaves, dormant type, broadly spreading.

*Height and spread*.—Reaches an average of 32.2 cm in height from soil level to top of foliar plane, 25 cm in height from soil level to top of floral plane, and 45.2 cm in spread.

*Cold hardiness*.—At least in U.S.D.A. Zone 5.

*Diseases and pests*.—No susceptibility or resistance to diseases or pests has been observed.

*Root description*.—Fleshy with fibrous secondary roots.

*Propagation type*.—Division.

*Root development*.—About 16 weeks to produce a salable young plant from a single fan division.

*Growth rate*.—Moderately vigorous.

Foliage description:

*Leaf shape*.—Linear.

*Leaf division*.—Simple.

*Leaf base*.—Decurrent.

*Leaf apex*.—Acute with a mucronate outer tip.

*Leaf venation*.—Parallel, color upper surface; 143A, color lower surface; NN137A and 147A.

*Leaf margins*.—Entire.

*Leaf attachment*.—Decurrent, no petioles.

*Leaf arrangement*.—Basal rosette.

*Leaf orientation*.—Held upright to pendulant.

*Leaf surface*.—Both surfaces glabrous, upper surface moderately glossy, lower surface matte.

*Leaf color*.—Young leaves upper surface; a blend of 137B and 143A, young leaves lower surface; 143A and 144A, mature leaves upper surface; a blend of NN137A and 147A, covered with a very thin waxy layer of 189A, mature lower surface; NN137A and NN137C, covered with a very thin waxy layer of 189A.

*Leaf size*.—Up to 39.8 cm in length, an average of 1 cm in width.

*Leaf quantity*.—Average of 8 per rosette, 10 leaves per shoot.

Flower description:

*Inflorescence type*.—Scape bearing a panicle of single flowers.

*Inflorescence size*.—7.2 cm (excluding peduncle), 6.8 cm in diameter.

*Lastingness of flowers*.—Average of 1 day, self-cleaning.

*Flower size*.—An average of 6.7 cm in height and diameter, 6.4 cm in depth, throat; 5.5 mm in diameter, tube; 1.5 cm in length, 6 mm in diameter.

*Flower fragrance*.—None.

*Flower number*.—Average of 4 per inflorescence, 19 flower buds per plant.

*Flower aspect*.—Upright to outward.

*Flower type*.—Campanulate, freely flowering.

*Flower bud*.—Narrow oblong in shape, average of 3.6 cm in length and 1.1 cm in width, moderately glossy, smooth, glabrous, color 151A, central section 175B, base 144A to 144B, tip 143B.

*Petals* (*inner tepals*).—3, obovate in shape, strongly reflexed, average of 6.4 cm in length and 3.1 cm in width, margins entire, moderately to highly finely undulate, upper half of free portion revolute, apex broadly retuse, base fused (lower 22%), upper surface smooth, glabrous, velvety, matte, lower surface smooth, glabrous, very slightly glossy, color: upper surface when opening and fully open; 178C, margins 178B, base 13B, tube 151A, veins 12D, lower surface when opening and fully open; 173C, broad margins 176C, base 148B, tube N144B, veins 173C, flower throat color; 151A, flower throat vein color; 12D, flower tube color; N144A.

*Sepals* (*outer tepals*).—3, rotate in arrangement, average of 5.7 cm in length, 2.3 cm in width, obovate in shape upper half moderately reflexed, margins are entire and moderately to highly finely undulate, upper half of free portion revolute, apex broadly retuse, base 24.5% fused, apex is broadly acute with an abruptly acute tip, upper surface texture is smooth, glabrous, velvety and matte, lower surface texture is smooth, glabrous and very slightly glossy, color: when opening and fully open upper surface; upper ⅗th of sepal 178C, margins 178B, lower ⅖th of sepal 13B, tube 151A, outer tip 6B, opening and fully open lower surface; N170A, broadly margined N170B, base 14B, tube 151A, outer tip 151D.

*Peduncles*.—Smooth and glabrous surface, round in shape, average of 20 cm in length, 3 mm in diameter, strong in strength, held in an average angle of 10°, strong in strength, color 137A, covered with a thin waxy layer N138D, bracts; average of 1 per peduncle, broadly lanceolate in shape, cuneate base, acuminate apex, margins entire with slight notch on each side, an average of 2.7 cm in length and 1.5 cm in width, color 155B at base and blending with 144A in towards apex.

*Pedicels*.—Smooth and glabrous surface, round in shape, average of 3 mm in length, 2 mm in diameter, strong in strength, held in an average angle of 35°, strong in strength, color 143A to 143B.

Reproductive organs:

*Gynoecium*.—Pistil; 1, average of 5.7 cm in length, style; 5.65 cm in length, color; 166C, proximal end 22B to 22D, stigma; crested, 11D in color, 0.05 mm in length and diameter, ovary; oblong in shape, 143C in color.

*Androecium*.—Stamens; 6, anthers; dorsifixed and narrow oblong in shape, 6 mm in length, 2 mm in width, 22A in color; filament; 2.9 cm in length, color; 164A, proximal end 15B, pollen; abundant in quantity and 17A in color.

*Fruit/seeds*.—None observed to date.

It is claimed:

1. A new and distinct cultivar of *Hemerocallis* plant named 'VER00330' as herein illustrated and described.

* * * * *